United States Patent [19]

Muchowski et al.

[11] 4,347,186
[45] Aug. 31, 1982

[54] PROCESS FOR PREPARING 5-AROYL 1,2-DIHYDRO-3-H PYRROLO[1,2-A]PYRROLE-1-CARBOXYLIC ACIDS AND NOVEL INTERMEDIATES THEREIN

[75] Inventors: Joseph M. Muchowski, Sunnyvale, Calif.; Robert Greenhouse, Mexico City, Mexico

[73] Assignee: Syntex (U.S.A.) Inc., Palo Alto, Calif.

[21] Appl. No.: 198,552

[22] Filed: Oct. 20, 1980

[51] Int. Cl.³ .................. A61K 31/40; C07D 209/00; C07D 487/04
[52] U.S. Cl. ................................. 548/516; 424/274; 548/468; 548/517; 548/539; 548/560
[58] Field of Search ............ 260/326.25, 326.2, 326.31

[56] References Cited
U.S. PATENT DOCUMENTS
4,089,969  5/1978  Muchowski et al. .......... 260/326.25

Primary Examiner—Alton D. Rollins
Attorney, Agent, or Firm—Tom M. Moran; Alan M. Krubiner

[57] ABSTRACT

5-Substituted-1,2-dihydro-3H-pyrrolo[1,2-a]pyrrole-1-carboxylic acids of the formula

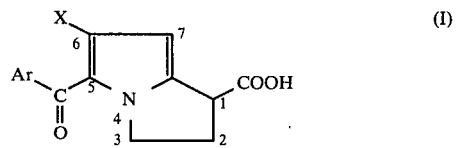

wherein:
X is hydrogen or lower alkyl; Ar is a moiety selected from the group consisting of

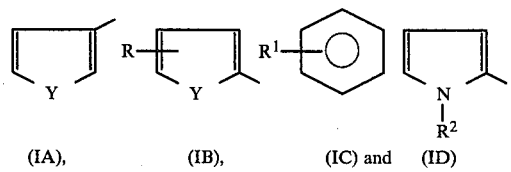

(IA),    (IB),    (IC) and    (ID)

in which:
Y is oxygen or sulfur;
R is hydrogen, methyl, chloro, or bromo, the R substitution being at the 3, 4 or 5 position of the ring;
$R^1$ is hydrogen, lower alkyl, lower alkoxyl, lower alkoxycarbonyl, lower alkylcarbonyl, fluoro, chloro or bromo, the $R^1$ substitution being at any available position in the ring;
$R^2$ is hydrogen or lower alkyl;
are prepared by β-decarboxylation of the corresponding dialkyl-1,1-dicarboxylates. Certain substituted pyrroles are useful as intermediates for preparing the compounds of formula I.

35 Claims, No Drawings

PROCESS FOR PREPARING 5-AROYL 1,2-DIHYDRO-3-H PYRROLO[1,2-A]PYRROLE-1-CARBOXYLIC ACIDS AND NOVEL INTERMEDIATES THEREIN

BACKGROUND OF THE INVENTION

1. Field of the Invention

This invention relates to a process for preparing 5-aroyl-1,2-dihydro-3H-pyrrolo-[1,2-a]pyrrole-1-carboxylic acids of the formula

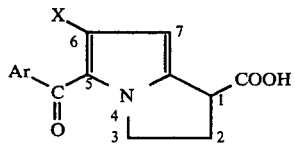

by decarboxylation of the corresponding 1,1-dicarboxylates. This invention also related to a process for the preparation of the 1,1-dicarboxylates and novel intermediates therein.

2. Prior Art

The "end-products" of Formula (I) with the exception of those wherein $R^1$ is carboxyl, lower alkoxycarbonyl or lower alkylcarbonyl, have been previously described. The Ar moiety, as will be described herein below, is shown as

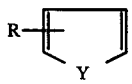 (partial formula (IA) and (IB)), in U.S. Pat. No. 4,087,539, as

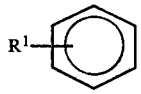, (partial formula (IC))

in U.S. Pat. No. 4,089,969, and as

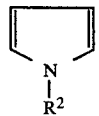 (partial formula (ID))

and U.S. Pat. No. 4,097,579. The preparation of the above is disclosed by methods other than those disclosed herein.

The compounds of Formula (I) are useful as anti-inflammatory agents, analgesic agents, platelet aggregation inhibitors, fibrinolytic agents, and as smooth muscle relaxants. They can be used both prophylactically and therapeutically, as disclosed in U.S. Pat. Nos. 4,087,539, 4,089,969, and 4,097,579 which are incorporated herein by reference.

SUMMARY OF THE INVENTION

One aspect of the invention herein relates to preparation of the compounds of Formula (I) by decarboxylating the corresponding dialkyl 5-substituted-1,2-dihydro-3H-pyrrolo[1,2-a]pyrrole-1,1-dicarboxylates of the formula

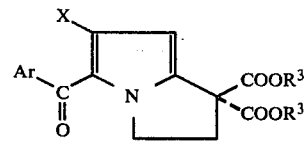

wherein:

X is hydrogen or lower alkyl; Ar is a moiety selected from the group consistig of

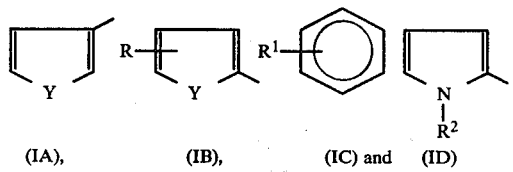

in which:

Y is oxygen or sulfur;

R is hydrogen, methyl, chloro, or bromo, the R substitution being at the 3, 4 or 5 position of the ring;

$R^1$ is hydrogen, lower alkyl, lower alkoxycarboxyl, lower alkoxycarbonyl, lower alkylcarbonyl, fluoro, chloro or bromo, the $R^1$ substitution being at any available position in the ring;

$R^2$ is hydrogen or lower alkyl;

and $R^3$ is hydrogen or lower alkyl, to compounds of Formula I, by treating them with acid or preferably by treating with base and subsequently treating with acid. Said conversion may be represented schematically:

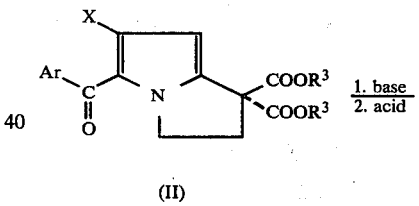

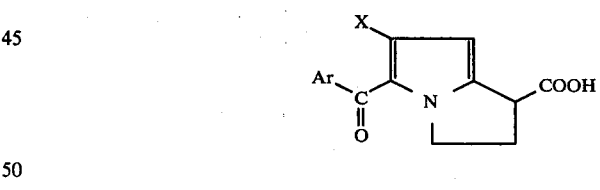

Another aspect of this invention relates to overall synthesis of compounds of formula I and preparation of compounds of formula II.

The intermediate compounds in said overall process are new. Therefore, in another aspect, the present invention relates to these novel compounds, which are useful as intermediates in the process herein and are set forth below.

DETAILED DESCRIPTION OF THE INVENTION

Definitions

As used herein, "lower alkyl" means a branched or unbranched saturated hydrocarbon chain containing from one to four carbon atoms;

"lower alkoxyl" means —OR wherein R is lower alkyl as herein defined;

"lower alkoxycarbonyl" means

wherein R is lower alkyl as herein defined;

"lower alkylcarbonyl" means

wherein R is lower alkyl as herein defined;

"strong mineral acid" means an inorganic water soluble, easily dissociable Bronsted Lowry acid, such as hydrochloric, sulfuric, phosphoric and the like;

"strong mineral base" means an inorganic water soluble, base with a $pk_b$ less than about 5, such as sodium hydroxide, sodium carbonate, potassium bicarbonate and the like.

"optionally substituted phenyl" means a phenyl group which may or may not be substituted with a moiety selected from the group consisting of halo and lower alkyl.

PREPARATION OF COMPOUNDS OF FORMULA II

A schematic of the conversion of compounds of Formula A, i.e. pyrrole or the 3-lower alkyl or 3-halo pyrroles to compounds of Formula II is shown in Reaction Scheme I

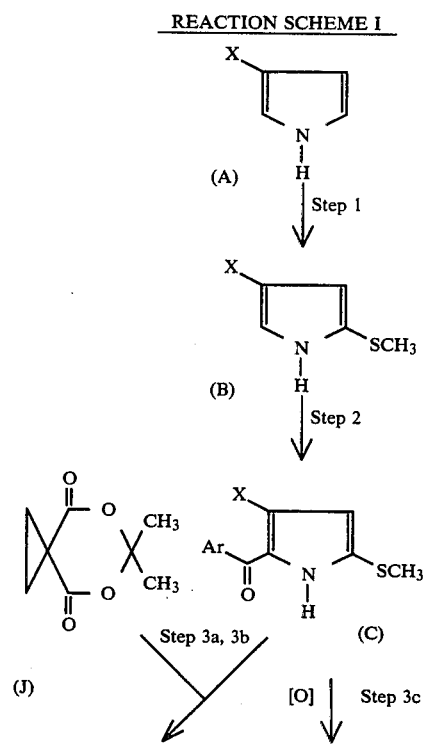

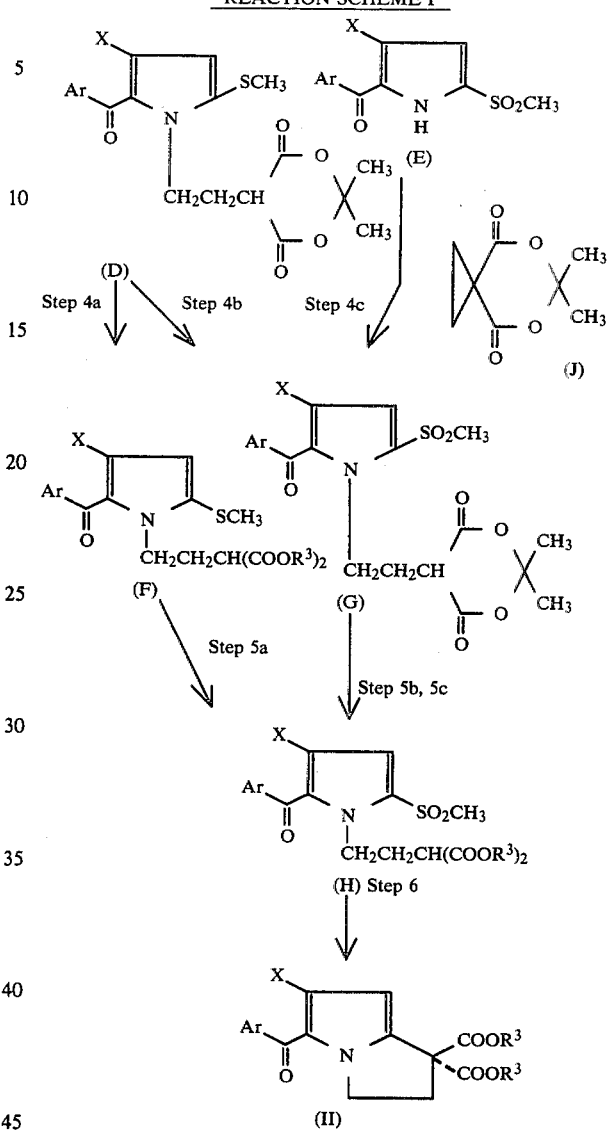

The intermediates B through H may be isolated, if desired, using conventional techniques, including but not limited to, filtration, distillation, crystallization, chromatography and the like as stated hereinabove. Such intermediates may be characterized using conventional means, including physical constants and spectral characteristics.

As seen from Reaction Scheme I, the process is congruent in Steps 1 and 2, but diverges at compounds of Formula C into 3 alternative pathways, a, b and c (which, at times overlap) and then converges to a common intermediate at compounds of Formula H. Step 6 is then congruent with respect to these alternatives.

Preparation of compounds of Formula B, accomplished herein in Step 1, has been described elsewhere: Matteson et al, *J. Org. Chem.* 22:1500 (1957); Japanese Pat. No. 53/025,559.

However, in the present invention, improved yields were obtained by a new process which comprises treating the appropriate pyrrole or 3-alkyl pyrrole with a reagent formed from dimethylsulfide and an N-halosucinimide.

(Other dialkyl sulfides may also be used, but there is no advantage to doing so, as the alkyl sulfide group will be lost during the subsequent steps in the process.)

In this conversion, an N-halosuccinimide, preferably N-chlorosuccinimide, dissolved in a non-polar aprotic solvent, preferably dichloromethane, is treated with an approximately equimolar amount of dimethylsulfide, also so dissolved. The treatment is accomplished slowly, preferably dropwise, and the reaction mixture thereby maintained at low temperature (about −10° to +5°, preferably 0° to +5°).

When the reagent preparation described above is complete, the solution is cooled to about −50° to −20°, preferably to −35° to −25°, allowed to stand for 10 minutes to 3 hours, preferably about 1 hour, and then an approximately equimolar amount of the pyrrole starting material of formula A also dissolved in the above solvent is slowly added. The reaction mixture may be allowed to stand at this low temperature for about 10 minutes to 3 hours, preferably about 1 hour, and the temperature is then allowed to rise to room temperature, preferably 20°. Solvent is removed by evaporation, and product is formed by either heating in vacuo and collecting product as distillation occurs, or by heating in the presence of solvent and collecting the product by subsequent distillation.

In Step 2, the process used is substantially that described in U.S. Pat. Nos. 4,087,539; 4,089,969 and 4,097,579, which are incorporated herein by reference. The procedures as described therein may be modified by using other dialkylamines, such as methyl ethyl amine, ethyl n-propyl amine and the like to form the aroylamides. The resulting aroylamides may then be substituted for the aroyldimethylamides in the same procedures. Additionally, aroyl halides may be used directly, obviating the need for phosphorous oxychloride or other analogous halogenating agent. However, the resulting compounds of Formula C are new.

Steps 3a, 3b and 4c are each effected in the same manner as each other. The subject pyrrole derivative is treated with an excess of an alkali metal hydride or other strong base, preferably sodium hydride under an inert atmosphere e.g. nitrogen, neon or argon, preferably argon, until reaction is complete. This time may range from 10 minutes to 10 hours, but is ordinarily in the range of 1-2 hours. The reaction takes place at about 0°-40°, but preferably at room temperature i.e. 15°-25°. Operable solvents include any aprotic organic polar solvent, e.g., DME, diglyme, DMF and the like; preferably DMF.

After the treatment with the hydride, compound J, i.e. spiro[2,5]-5,7-dioxa-6,6-dimethyloctane-4,8-dione, prepared according to Singh et al, *J. Org. Chem.* 40: 2969 (1975) is added in slight excess and the temperature is raised to about 40°-80°, preferably 50°-60°, and the mixture is allowed to react for about 1-10 hours or to completion. The product, a compound of Formula D (Steps 3a or 3b) or Formula G (Step 4c) may be isolated, preferably as the salt.

Analogous spiro cyclopropyl compounds, with the general formula

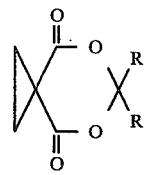

wherein each R may independently be lower alkyl, may also be used. These compounds may be prepared in a manner similar to that for spiro[2,5]-5,7-dioxa-6,6-dimethyloctane-4,8-dione by substituting other ketones for acetone to form the dioxyketal ring. Thus, for example, spiro[2,5]-5,7-dioxa-6,6-diethyl-octane-4,8-dione;

spiro[2,5]-5,7-dioxa-6-methyl-6-ethyl-octane-4,8-dione, and 2-spiro[2,5]-5,7-dioxa-6-methyl-6-propyl-octane-4,8-dione, may be prepared using 3-pentanone, methyl ethyl ketone (2-butanone) and 2-pentanone respectively. However, there is no particular advantage in varying the 6,6-substitution, since subsequent steps in the overall process remove these groups, and ease of removal is not enhanced by such variation. Therefore, the preferred method is to employ spiro[2,5]-5,7-dioxa-6,6-dimethyloctane-4,8-dione.

Steps 4a, 5b and 5c are carried out similarly to each other. In each case the cyclic diester dissolved in a suitable solvent, e.g. an alcohol, is converted to the corresponding dialkyl dicarboxylate or dicarboxylic acid by treatment with a suitable alcohol in the presence of acid. In a preferred embodiment the subject compound is dissolved in methanol and treated with methanol previously saturated with HCl at about 25°-80°, preferably 60°-70° for about 5 minutes to 5 hours, preferably 10 minutes to 40 minutes. The dimethyl or other dialkyl ester may then be recovered by suitable conventional techniques.

Steps 5a, 3c, and 4b all represent the oxidation of the methyl thiopyrrole to the methyl sulfonylpyrrole. An excess of oxidizing agent, e.g. peroxide, permanganate, or peracid preferably m-chloroperbenzoic acid in excess, and preferably in an approximately 2:1 molar ratio to the subject compound is used. The reaction can be done at low temperature, about −10° to +15°, preferably 0° C. in a non-polar, aprotic organic solvent, e.g. chloroform, dichloromethane or dichloroethane, preferably dichloromethane. The reaction time may vary from about 15 minutes to 10 hours; usually it is in the range of 2-3 hours. The product is then recovered using techniques familiar to those skilled in the art.

The sequences 3a, 4a, 5a; 3b, 4b, 5b; and 3c, 4c, 5c all converge at compounds of formula H, the 1-(2-ethylmalonate) derivative of the 5-aroyl pyrrole. Cyclization to the corresponding pyrrolo[1,2-a]pyrrole compound of Formula II takes place in step 6.

To carry out step 6, the subject compound is dissolved in an aprotic organic polar solvent, preferably dimethylformamide and treated with a slight excess of an alkali metal hydride, preferably sodium hydride in mineral oil. The reaction mixture may be heated to about 50°-150° for about 10 minutes to 10 hours, preferably to 100°-110° for 4-6 hours. All of these operations are carried out in an inert atmosphere, preferably under nitrogen. The mixture is then cooled to about 5°-40°, preferably room temperature (15°-25°) and the solution made acidic, preferably by addition of 10% hydrochloric acid. The product of Formula II may then be recovered.

The compounds of Formula II are then converted to the corresponding 5-aroyl-1,2-dihydro-3H-pyrrolo[1,2-a]pyrrole-1-carboxylic acids as described hereinbelow.

THE CONVERSION OF COMPOUNDS OF FORMULA II TO COMPOUNDS OF FORMULA I

The conversion herein consists of treatment with base to accelerate ester hydrolysis, followed by treatment with acid to effect decarboxylation.

In the special case where $R^3$ is hydrogen, treatment with base is unnecessary, and the conversion can be carried out in the presence of acid only. Where $R^3$ is lower alkyl, it is possible, but not particularly desirable to carry out the entire conversion under acid conditions; the preferred method is to hydrolyze the esters first by treatment with base, and then decarboxylate in acid.

The conditions of treatment with base and acid to effect hydrolysis and decarboxylation are familiar to those skilled in the art for decarboxylation of $\beta$-dicarboxylic acid esters. For hydrolysis under basic conditions, the use of a strong base, preferably a mineral base, e.g., potassium hydroxide, sodium hydroxide, lithium hydroxide, and the like, in the presence of water is preferred. Advantageously, water miscible organic solvents, e.g., 2-methoxyethanol, methanol, ethanol, ethylene glycol, dimethylsulfoxide, and the like are used to facilitate solution of the reactants. The reaction is peferably carried out under an inert atmosphere, e.g., nitrogen, argon, and the like, with nitrogen being the most preferred. The reaction times and temperatures are not critical and depend, as will be apparent to those skilled in the art, on the reactants (and other ingredients of the reaction mixture) employed. Thus the reaction time can be from about 5 minutes to about 2 hours, with 30 minutes to 1 hour being preferred; and the reaction temperature from about 60° C. to reflux temperature with 70° C. to reflux temperature being preferred.

Subsequent treatment with acid is effected preferrably with a strong mineral acid, e.g., phosphoric acid, sulfuric acid, hydrochloric acid, hydrobromic acid, and the like in the presence of water, with or without the presence of an organic acid, e.g., acetic acid, formic acid, propionic acid, and the like. If desired other organic solvents miscible with the mineral acid (and the water and the organic acid, if the latter is used) can be used. Suitable organic solvents are ethyl acetate, methanol, ethanol, ethylene glycol, dimethylsulfoxide, dioxane, tetrahydrofuran, ethylene glycol dimethyl ether (glyme), diethylene glycol dimethyl ether (diglyme), and the like. The reaction may be carried out under an inert atmosphere, e.g., nitrogen, argon, and the like, with nitrogen being the most preferred. The reaction times and temperatures are not critical and depend, as will be apparent to those skilled in the art, on the reactants and other ingredients of the reaction mixture) employed. Thus, the reaction time can be from instanteous to about 10 hours with one minute to 5 minutes being preferred; and the reaction temperature from about 10° C.–100° C., preferably 15°–30° C.

Isolation, separation, and purification of the desired compound of Formula (I) from the reaction mixture containing it can be effected by any suitable separation or purification procedure, such as, for example, extraction, filtration, evaporation, distillation, crystallization, thin-layer chromatography, or column chromatography, high pressure liquid chromatography, and the like, or a combination of these procedures. Illustrations of suitable isolation, separation and purification procedures can be had by reference to the Examples herein below. However, other isolation, separation and isolation procedures, could of course, also be used.

NOVEL INTERMEDIATES

The compounds of formula C, D, E, F, G, H and II are novel, and are useful as intermediates in preparing compounds of formula (I) which are therapeutically useful as discussed hereinbefore.

PREFERRED EMBODIMENTS

A set of preferred embodiments of the present invention is composed of those wherein the decarboxylation of the compounds of formula II is effected by treating said compounds with acid, especially strong mineral acid, or more preferably by treating said compounds with base, followed by acid, and most preferably with strong mineral base followed by strong mineral acid.

The sequences 1, 2, 3a, 4a, 5a, 6 and 1, 2, 3b, 4b, 5b, 6 in the preparation of the compound of formula II appear slightly superior to the sequence 1, 2, 3c, 4c, 5c, 6. However, the latter sequence is certainly perfectly practicable.

Another set of preferred embodiments is that wherein X is hydrogen or methyl and Ar is thien-2-yl, furan-2-yl, pyrrol-2-yl or optionally substituted phenyl.

The conversion of step 6 is best carried out by treating a compound of formula H with an alkali metal hydride in an aprotic solvent.

The conversions of steps 5a, 4b, and 3c are best carried out by treating compounds of formulas, F, D and C, respectively, with a perbenzoic acid.

The following examples illustrate the embodiment of the present invention, and should not be construed to limit it.

EXAMPLE 1

Preparation of 2-methylthiopyrrole (Step 1)

A. To a stirred solution of N-chlorosuccinimide (10.0 g, 0.075 moles) in dry dichloromethane (100 ml), cooled to 0°, was added a solution of dimethylsulfide (4.67 g, 0.075 moles) in dichloromethane (50 ml) at a rate such that the reaction temperature did not exceed 5°. When the addition was completed, the solution was cooled to −30° and pyrrole (5.04 g, 0.075 moles) was added slowly. The temperature was then allowed to rise to 20°, and the dichloromethane was removed in vacuo. The residue thus obtained was placed in a distillation flask and heated in vacuo in an oil bath. The fraction bp. 60°–65°/30 mm (41% yield), which contained the resulting 2-methylthiopyrrole was collected.

B. In a similar manner:
3-n-butylpyrrole,
3-i-propylpyrrole, and
3-methylpyrrole
may be converted to:
4-n-butyl-2-methylthiopyrrole,
4-i-propyl-2-methylthiopyrrole, and
4-methyl-2-methylthiopyrrole, respectively.

EXAMPLE 2

Preparation of 5-benzoyl-2-methylthiopyrrole (Step 2)

A solution of N,N-dimethylbenzamide (237 g) in anhydrous 1,2-dichloroethane (60 ml) containing phosphorous oxychloride (2.43 g) was boiled under reflux, in a nitrogen atmosphere, for 0.75 hour. To the cooled solution was added 2-methylthiopyrrole (0.9 g) in 1,2-dichloroethane (40 ml) and heating at reflux was recommenced and maintained for 1 hour. The reaction progress was followed by TLC [silica gel, dichloromethane-ethyl acetate (97:3)] which showed that the reaction was complete in 30 minutes. The reaction was cooled, sodium acetate (5.41 g) in water (80 ml) was added, and the mixture was heated at reflux temperature (nitrogen atmosphere) for 1.5 hours. The organic phase was separated, combined with a dichloromethane extract of the aqueous phase and the combined organic phases were washed with water and dried. The solvent was removed in vacuo and the residue was subjected to column chromatography on silica gel. The product was eluted with dichloromethane-hexane (1:1) and on crystallization from methanol, 2-methylthio-5-benzoylpyrrole (1.19 g, 79%), m.p. 106°–108°, was obtained with the following properties:

UV: (MeOH) 249, 340 nm(8510, 15,100).
IR: (CHCl$_3$) 3420, 3215, 1610, 1554, 1535 cm$^{-1}$.
NMR: (CDCl$_3$)

| | |
|---|---|
| 2.41 | (s, 1H) |
| 6.16 | (m, 1H) |
| 6.73 | (m, 1H) |
| 7.38 | (m, 3H) |
| 7.78 | (m, 2H) |
| 10.16 | (m, 1H) |

Calcd. for $C_{12}H_{11}NOS$: C, 66.33; H, 5.10; N, 6.44
Found: C, 66.58; H 5.10; N, 6.36

B. Substituting the 4-alkyl 2-methylthiopyrroles listed in part B of Example 1 for 2-methylthiopyrrole, and using a similar procedure to that in Part A of this example, one obtains, respectively,
  5-benzoyl-4-n-butyl-2-methylthiopyrrole,
  5-benzoyl-4-i-propyl-2-methylthiopyrrole, and
  5-benzoyl-4-methyl-2-methylthiopyrrole.

C. Substituting, in the procedure of Part A of this example, for N,N-dimethylbenzamide,
  N,N-dimethyl 3-thenoylamide,
  N,N-dimethyl 2-furoylamide,
  N,N-dimethyl 2-thenoylamide,
  N,N-dimethyl 3-chloro-2-furoylamide,
  N,N-dimethyl 4-bromo-2-furoylamide,
  N,N-dimethyl 5-methyl-2-furoylamide,
  N,N-dimethyl 4-methyl-2-thenoylamide,
  N,N-dimethyl 1-butyl-2-pyrroylamide,
  N,N-dimethyl 1-methyl-2-pyrroylamide,
  N,N-dimethyl 2-pyrroylamide,
  N,N-dimethyl 4-chlorobenzoylamide,
  N,N-dimethyl 3-methoxybenzoylamide,
  N,N-dimethyl 2-ethoxycarbonylbenzoylamide,
  N,N-dimethyl 2-fluorobenzoylamide,
  N,N-dimethyl 3-ethylbenzoylamide,
  N,N-dimethyl 4-n-ethylcarbonylbenzoylamide,
one obtains, respectively
  5-(3-thenoyl)-2-methylthiopyrrole,
  5-(2-furoyl)-2-methylthiopyrrole,
  5-(2-thenoyl)-2-methylthiopyrrole,
  5-(3-chloro-2-furoyl)-2-methylthiopyrrole,
  5-(4-bromo-2-furoyl)-2-methylthiopyrrole,
  5-(5-methyl-2-furoyl)-2-methylthiopyrrole,
  5-(4-methyl-2-thenoyl)-2-methylthiopyrrole,
  5-(1-butyl-2-pyrroyl)-2-methylthiopyrrole,
  5-(1-methyl-2-pyrroyl)-2-methylthiopyrrole,
  5-(2-pyrroyl)-2-methylthiopyrrole,
  5-(4-chlorobenzoyl)-2-methylthiopyrrole,
  5-(3-methoxybenzoyl)-2-methylthiopyrrole,
  5-(2-ethoxycarbonylbenzoyl)-2-methylthiopyrrole,
  5-(2-fluorobenzoyl)-2-methylthiopyrrole,
  5-(3-ethylbenzoyl)-2-methylthiopyrrole, and 5-(4-n-ethylcarbonylbenzoyl)-2-methylthiopyrrole.

EXAMPLE 3

Preparation of 1-[2-(4,6-dioxo-2,2-dimethyl-1,3-dioxan-5-yl)ethyl]-2-methylthio)-5-(benzoyl)pyrrole (Step 3a or 3b)

2-methylthio-5-benzoylpyrrole (0.741 g, 3.41 mmoles) was added to a suspension of 50% sodium hydride in mineral oil (0.177 g, 3.68 mmoles) in dry dimethylformamide (80 ml) maintained in an atmosphere of argon. After 1 hour at room temperature the formation of the anion was complete and compound J, spiro[2,5]-5,7-dioxa-6,6-dimethyloctane-4,8-dione (0.625 g, 3.68 mmoles) was added, and the solution was heated to 55°. After 5 hours, TLC (dioxan-dimethoxyethane acetic acid, 30:70:1) indicated that the reaction did not progress any further. The cooled solution was diluted with water (150 ml) and the starting material was extracted with ethyl acetate. The extract was dried over sodium sulfate and evaporated in vacuo to give the starting material (0.110 g, 15%). The aqueous phase from above was made acidic with 0.01 N hydrochloric acid and the product was extracted into ethyl acetate (2×100 ml). The extract was dried and evaporated in vacuo to give the crude product which was purified by column chromatography on silica gel (ethyl acetate-hexane; 1:1). There was thus obtained a solid, which after crystallization from ethyl acetate-hexane had characteristics, as indicated below of [1-[2-(4,6-dioxo-2,2-dimethyl-1,3-dioxan-5-yl)ethyl]-2-(methylthio)-5-(benzo yl)]pyrrole, (0.978 g. 74%) m.p. 124°–125°, UV: (MeOH) 216, 254, 339.5 nm($\epsilon$8510, 10,000, 14,000).
IR: (CHCl$_3$) 1795, 1755, 1615 cm$^{-1}$.

| | |
|---|---|
| 1.75 | (s, 3H) |
| 1.82 | (s, 3H) |
| 2.48 | (s, 3H) |
| 2.48–2.8 | (s, 3H) |
| 4.20 | (t, 1H; J = 6 Hz) |
| 4.73 | (t, 2H; J = 6) |
| 6.17 | (d, 1H; J = 4) |
| 6.72 | (d, 1H; J = 4) |
| 7.2–7.9 | (m, 5H) |

Calcd. for $C_{20}H_{21}NO_5S$: C, 62.00; H, 5.46.
Found: C, 62.01; H, 5.45.

B. In similar fashion, using the procedure outlined in A, above, and substituting for 2-methylthio-5-benzoylpyrrole the compounds listed in Example 2, part B, one obtains:
  [1-[2-(4,6-dioxo-2,2-dimethyl-1,3-dioxan-5-yl)ethyl]-2-methylthio)-5-(benzoyl)-4-n-butyl-]pyrrole,
  [1-[2-(4,6-dioxo-2,2-dimethyl-1,3-dioxan-5-yl)ethyl]-2-methylthio)-5-(benzoyl)4-i-propyl-]pyrrole, and
  [1-[2-(4,6-dioxo-2,2-dimethyl-1,3-dioxan-5-yl)ethyl]-2-methylthio)-5-(benzoyl)4-methyl-]pyrrole.

C. In similar manner, using the procedure of part A of this example, and substituting for 2-methylthio-5-benzoylpyrrole the compounds listed in Example 2, part C, one obtains
  [1-[2-(4,6-dioxo-2,2-dimethyl-1,3-dimethyl-1,3-dioxan-5-yl)ethyl]-2-methylthio-5-(3-thenoyl)]pyrrole,

[1-[2-(4,6-dioxo-2,2-dimethyl-1,3-dimethyl-1,3-dioxan-5-yl)ethyl]-2-methylthio-5-(2-furoyl)]pyrrole,
[1-[2-(4,6-dioxo-2,2-dimethyl-1,3-dimethyl-1,3-dioxan-5-yl)ethyl]-2-methylthio-5-(2-thenoyl)]pyrrole,
[1-[2-(4,6-dioxo-2,2-dimethyl-1,3-dimethyl-1,3-dioxan-5-yl)ethyl]-2-methylthio-5-(3-chloro-2-furoyl)]pyrrole,
[1-[2-(4,6-dioxo-2,2-dimethyl-1,3-dimethyl-1,3-dioxan-5-yl)ethyl]-2-methylthio-5-(4-bromo-2-furoyl)]pyrrole,
[1-[2-(4,6-dioxo-2,2-dimethyl-1,3-dimethyl-1,3-dioxan-5-yl)ethyl]-2-methylthio-5-(5-methyl-2-furoyl)]pyrrole,
[1-[2-(4,6-dioxo-2,2-dimethyl-1,3-dimethyl-1,3-dioxan-5-yl)ethyl]-2-methylthio-5-(4-methyl-2-thenoyl)]pyrrole,
[1-[2-(4,6-dioxo-2,2-dimethyl-1,3-dimethyl-1,3-dioxan-5-yl)ethyl]-2-methylthio-5-(1-butyl-2-pyrroyl)]pyrrole,
[1-[2-(4,6-dioxo-2,2-dimethyl-1,3-dimethyl-1,3-dioxan-5-yl)ethyl]-2-methylthio-5-(1-methyl-2-pyrrolyl)]pyrrole,
[1-[2-(4,6-dioxo-2,2-dimethyl-1,3-dimethyl-1,3-dioxan-5-yl)ethyl]-2-methylthio- 5-(2-pyrroyl)]pyrrole,
[1-[2-(4,6-dioxo-2,2-dimethyl-1,3-dimethyl-1,3-dioxan-5-yl)ethyl]-2-methylthio-5-(4-chlorobenzoyl)]pyrrole,
[1-[2-(4,6-dioxo-2,2-dimethyl-1,3-dimethyl-1,3-dioxan-5-yl)ethyl]-2-methylthio-5-(3-methoxybenzoyl)]pyrrole,
[1-[2-(4,6-dioxo-2,2-dimethyl-1,3-dimethyl-1,3-dioxan-5-yl)ethyl]-2-methylthio-5-(2-ethoxycarbonylbenzoyl)]pyrrole,
[1-[2-(4,6-dioxo-2,2-dimethyl-1,3-dimethyl-1,3-dioxan-5-yl)ethyl]-2-methylthio-5-(2-fluorobenzoyl)]pyrrole,
[1-[2-(4,6-dioxo-2,2-dimethyl-1,3-dimethyl-1,3-dioxan-5-yl)ethyl]-2-methylthio-5-(3-ethylbenzoyl)]pyrrole,
[1-[2-(4,6-dioxo-2,2-dimethyl-1,3-dimethyl-1,3-dioxan-5-yl)ethyl]-2-methylthio-5-(4-ethylcarbonylbenzoyl)]pyrrole.

EXAMPLE 4

Preparation of [1-[2-(4,6-dioxo-2,2-dimethyl-1,3-dioxan-5-yl)ethyl]-2-methanesulfonyl)-5-(benzoyl)]pyrrole (Step 4b)

To a solution of [1-[2-(4,6-dioxo-2,2-dimethyl-1,3-dioxan-5-yl)ethyl]-2-methylthio)-5-(benzoyl)]pyrrole (0.500 g, 1.29 mmoles) in dry dichloromethane (100 ml), cooled in an ice bath, was added 85% m-chloroperbenzoic acid (0.600 g, 3.47 mmoles). The reaction was followed by TLC (ethyl acetate-hexane); 1:1 on silica gel. Two spots, more polar than the starting material, were observed. The most polar corresponded to the sulfoxide and the other to the sulfone. After three hours at this temperature, the solvent was evaporated in vacuo, and the solid residue was washed with ether to remove m-chlorobenzoic acid to leave a solid (0.486 g, 90%) with m.p. 154°–155° (dec.). After crystallization from aqueous acetone the product was shown to be, [1-[2-(4,6-dioxo-2,2-dimethyl-1,3-dioxan-5-yl)ethyl]-2-(methanesulfonyl)-5-(benzoyl)]-pyrrole, m.p. 159° (dec.).

UV: (MeOH) 260, 292, nm($\epsilon$ 10,200, 16,900).
IR: (KBr) 1787, 1742, 1645 cm$^{-1}$.
NMR: (DMSO d$_6$) or (Pyridine d$_5$)

| | |
|---|---|
| 1.67 | (s, 6H) |
| 3.05 | (t, 2H; J = 6.5 Hz) |
| 3.60 | (s, 3H) |
| 5.32 | (t, 2H; J = 6.5) |
| 6.62 | (d, 1H; J = 4) Pyridine-d$_5$ |
| 6.83 | (d, 1H; J = 4) DMSO-d$_6$ |
| 7.4–7.9 | (m, 5H) |

The methine proton was not clearly visible in either solvent.

Calcd. for C$_{20}$H$_{21}$NO$_7$S: C, 57.28; H, 5.05; N, 3.34. Found: C, 57.20; H, 5.25; N, 3.29.

B. Similarly, substituting for 1-[2-(4,6-dioxo-2,2-dimethyl-1,3-dioxan-5-yl)ethyl]-2-methyl(-lthio)-5-(benzoyl) pyrrole the compounds of Example 3, part B, one obtains

[1-[2-(4,6-dioxo-2,2-dimethyl-1,3-dioxan-5-yl)ethyl]-2-(methanesulfonyl)-4-(n-butyl)-5-(benzoyl)]pyrrole,
[1-[2-(4,6-dioxo-2,2-dimethyl-1,3-dioxan-5-yl)ethyl]-2-(methanesulfonyl)-4-(i-propyl)-5-(benzoyl)]pyrrole,
[1-[2-(4,6-dioxo-2,2-dimethyl-1,3-dioxan-5-yl)ethyl]-2-(methanesulfonyl)-4-(methyl)-5-(benzoyl)]pyrrole.

C. Substituting for 1-[2-(4,6-dioxo-2,2-dimethyl-1,3-dioxan-5-yl)ethyl]-2-methylthio)-5-(benzoyl) pyrrole the compounds of Example 3, part C, one obtains:

[1-[2-(4,6-dioxo-2,2-dimethyl-1,3-dioxan-5-yl)ethyl]-2-(methanesulfonyl)-5-(3-thenoyl)]pyrrole,
[1-[2-(4,6-dioxo-2,2-dimethyl-1,3-dioxan-5-yl)ethyl]-2-(methanesulfonyl)-5-(2-furoyl)]pyrrole,
[1-[2-(4,6-dioxo-2,2-dimethyl-1,3-dioxan-5-yl)ethyl]-2-(methanesulfonyl)-5-(2-thenoyl)]pyrrole,
[1-[2-(4,6-dioxo-2,2-dimethyl-1,3-dioxan-5-yl)ethyl]-2-(methanesulfonyl)-5-(3-chloro-2-furoyl)]pyrrole,
[1-[2-(4,6-dioxo-2,2-dimethyl-1,3-dioxan-5-yl)ethyl]-2-(methanesulfonyl)-5-(4-bromo-2-furoyl)]pyrrole,
[1-[2-(4,6-dioxo-2,2-dimethyl-1,3-dioxan-5-yl)ethyl]-2-(methanesulfonyl)-5-(5-methyl-2-furoyl)]pyrrole,
[1-[2-(4,6-dioxo-2,2-dimethyl-1,3-dioxan-5-yl)ethyl]-2-(methanesulfonyl-5-(4-methyl-2-thenoyl)]pyrrole,
[1-[2-(4,6-dioxo-2,2-dimethyl-1,3-dioxan-5-yl)ethyl]-2-(methanesulfonyl)-5-(1-butyl-2-pyrroyl)]pyrrole,
[1-[2-(4,6-dioxo-2,2-dimethyl-1,3-dioxan-5-yl)ethyl]-2-(methanesulfonyl)-5-(1-methyl-2-pyrroyl)]pyrrole,
[1-[2-(4,6-dioxo-2,2-dimethyl-1,3-dioxan-5-yl)ethyl]-2-(methanesulfonyl)-5-(2-pyrroyl)]pyrrole,
[1-[2-(4,6-dioxo-2,2-dimethyl-1,3-dioxan-5-yl)ethyl]-2-(methanesulfonyl)-5-(4-chlorobenzoyl)]pyrrole,
[1-[2-(4,6-dioxo-2,2-dimethyl-1,3-dioxan-5-yl)ethyl]-2-(methanesulfonyl)-5-(3-methoxybenzoyl)]pyrrole,
[1-[2-(4,6-dioxo-2,2-dimethyl-1,3-dioxan-5-yl)ethyl]-2-(methanesulfonyl)-5-(2-ethoxycarbonylbenzoyl)]pyrrole,
[1-[2-(4,6-dioxo-2,2-dimethyl-1,3-dioxan-5-yl)ethyl]-2-(methanesulfonyl)-5-(2-fluorobenzoyl)]pyrrole,
[1-[2-(4,6-dioxo-2,2-dimethyl-1,3-dioxan-5-yl)ethyl]-2-(methanesulfonyl)-5-(3-ethylbenzoyl)]pyrrole,
[1-[2-(4,6-dioxo-2,2-dimethyl-1,3-dioxan-5-yl)ethyl]-2-(methanesulfonyl)-5-(4-ethylcarbonylbenzoyl)]pyrrole.

EXAMPLE 5

Preparation of [1-[3,3-(dimethoxycarbonyl)propyl]-2-methanesulfonyl)-5-(benzoyl)]pyrrole (Steps 5b, 5c)

To a solution of [1-[2-(4,6-dioxo-2,2-dimethyl-1,3-dioxan-5-yl)ethyl]-2-(methanesulfonyl)-5-(benzoyl)-

]pyrrole (0.419 g) in methanol (25 ml) was added methanol (25 ml) which had been saturated with hydrogen chloride gas. The resultant mixture was heated at reflux for 0.5 hour, the progress of reaction being followed by TLC (ethyl acetate-hexane; 1:3) on silica gel. The solvent was removed in vacuo and the residue was percolated through a column of silica gel using ethyl acetate-hexane (1:4) as the percolating solvent. A viscous oil [1-[3,3-(dimethoxycarbonyl)propyl]-2-methanesulfonyl)-5-(benzoyl)]pyrrole (0.386 g, 95%) was obtained.

UV: (MeOH) 220, 261, 292.5 nm ($\epsilon$ 7590, 10,700 1590).

IR: (CHCl$_3$) 1755, 1740, 1650 cm$^{-1}$.

NMR: (CDCl$_3$).

| | |
|---|---|
| 2.48 | (m, 2H) |
| 3.22 | (s, 3H) |
| 3.55 | (t, 1H) |
| 3.72 | (s, 6H) |
| 4.80 | (m, 2H) |
| 6.67 | (d, 1H; J = 4Hz) |
| 6.88 | (d, 1H; J = 4) |
| 7.3–7.9 | (M, 5H) |

Calcd. for C$_{19}$H$_{21}$NO$_7$S: C, 56.01; H, 5.19; N, 3.43. Found: C, 55.87; H, 5.25; N, 3.24.

B. Substituting into the procedure of Part A for 1-[2-(4,6-dioxo-2,2-dimethyl-1,3-dioxan-5-yl)ethyl]-2-methanesulfonyl)-5-(benzoyl) pyrrole the compounds listed in Example 4, part B, one obtains:
[1-[3,3-dimethoxycarbonyl)propyl]-2-(methanesulfonyl)-4-(n-butyl)-5-benzoyl)]pyrrole,
[1-[3,3-(dimethoxycarbonyl)propyl]-2-(methanesulfonyl)-4-(i-propyl)-5-benzoyl)]pyrrole,
[1-[3,3-(dimethoxycarbonyl)propyl]-2-(methanesulfonyl)-4-(methyl)-5-benzoyl)]pyrrole.

C. Substituting into the procedure of Part A for 1-[2-(4,6-dioxo-2,2-dimethyl-1,3-dioxan-5-yl)ethyl]-2-methanesulfonyl)-5-(benzoyl) pyrrole the compounds listed in Example 4, part C, one obtains:
[1-[3,3-(dimethoxycarbonyl)propyl]-2-(methanesulfonyl)-5-(3-thenoyl)]pyrrole,
[1-[3,3-(dimethoxycarbonyl)propyl]-2-(methanesulfonyl)-5-(2-furoyl)]pyrrole,
[1-[3,3-(dimethoxycarbonyl)propyl]-2-(methanesulfonyl)-5-(2-thenoyl)]pyrrole,
[1-(3,3-(dimethoxycarbonyl)propyl]-2-(methanesulfonyl)-5-(3-chloro-2-furoyl)]pyrrole,
[1-[3,3-(dimethoxycarbonyl)propyl]-2-(methanesulfonyl)-5-(4-bromo-2-furoyl)]pyrrole,
[1-[3,3-(dimethoxycarbonyl)propyl]-2-(methanesulfonyl)-5-(5-methyl-2-furoyl)]pyrrole,
[1-[3,3-(dimethoxycarbonyl)propyl]-2-(methanesulfonyl)-5-(4-methyl-2-thenoyl)]pyrrole,
[1-[3,3-(dimethoxycarbonyl)propyl]-2-(methanesulfonyl)-5-(1-butyl-2-pyrroyl)]pyrrole,
[1-[3,3-(dimethoxycarbonyl)propyl]-2-(methanesulfonyl)-5-(1-methyl-2-pyrroyl)]pyrrole,
[1-[3,3-(dimethoxycarbonyl)propyl]-2-(methanesulfonyl)-5-(2-pyrroyl)]pyrrole,
[1-[3,3-(dimethoxycarbonyl)propyl]-2-(methanesulfonyl)-5-(4-chlorobenzoyl)]pyrrole,
[1-[3,3-(dimethoxycarbonyl)propyl-2-(methanesulfonyl)-5-(3-methoxybenzoyl)]pyrrole,
[1-[3,3-(dimethoxycarbonyl)propyl]-2-(methanesulfonyl)-5-(2-ethoxycarbonylbenzoyl)]pyrrole,
[1-[3,3-(dimethoxycarbonyl)propyl]-2-(methanesulfonyl)-5-(2-fluorobenzoyl)]pyrrole,
[1-[3,3-(dimethoxycarbonyl)propyl]-2-(methanesulfonyl)-5-(3-ethylbenzoyl)]pyrrole,
[1-[3,3-(dimethoxycarbonyl)propyl]-2-(methanesulfonyl)-5-(4-ethylcarbonylbenzoyl)]pyrrole.

EXAMPLE 6

Preparation of 2-methylsulfonyl-5-benzoylpyrrole (Step 3c)

A. A solution of 2-methylthio-5-benzoylpyrrole (0.300 g, 1.38 mmoles) and m-chloroperbenzoic acid (0.550 g; 86%, 3.18 mmoles) in anhydrous dichloromethane (50 ml) was stirred at 5° C. for 3 hours. The solution was extracted with 20% sodium carbonate solution, the organic phase was separated, dried over sodium sulfate and evaporated in vacuo. The residue was crystallized from acetone-hexane 2-methylsulfonyl-5-benzoylpyrrole (0.320 g, 100%)

mp: 148°–150° (acetone-hexane)

UV: 258, 294 nm ($\epsilon$ 8710, 16,600)

IR: (CHCl$_3$) 11047 3565, 3410, 3255, 1640, 1604, 1580 cm$^{-1}$

NMR: (CDCl$_3$)

| | |
|---|---|
| 3.22 | (s, 3H) |
| 6.86 | (s, 1H) |
| 6.90 | (s, 1H) |
| 7.40–7.60 | (m, 3H) |
| 7.82–8.00 | (m, 2H) |
| 11.10 | (s, 1H, W$_H$ = 16 Hz) |

MS: 249 (M+)

Calcd. for C$_{12}$H$_{11}$No$_3$S: C, 57.81; H, 4.45; N, 5.60. Found: C, 58.51; H, 4.34; N, 5.64

B. Similarly, substituting into the procedure of part A for 2-methylthio-5-benzoylpyrrole the compounds listed in Example 2, part B, one obtains:
2-methylsulfonyl-4-n-butyl-5-benzoylpyrrole,
2-methylsulfonyl-4-i-propyl-5-benzoylpyrrole, and
2-methylsulfonyl-4-methyl-5-benzoylpyrrole.

C. Similarly, substituting into the procedure of part A for 2-methylthio-5-benzoylpyrrole the compounds listed in Example 2, part C, one obtains:
2-methylsulfonyl-5-(3-thenoyl)pyrrole,
2-methylsulfonyl-5-(2-furoyl)pyrrole,
2-methylsulfonyl-5-(2-thenoyl)pyrrole,
2-methylsulfonyl-5-(3-chloro-2-furoyl)pyrrole,
2-methylsulfonyl-5-(4-bromo-2-furoyl)pyrrole,
2-methylsulfonyl-5-(5-methyl-2-furoyl)pyrrole,
2-methylsulfonyl-5-(4-methyl-2-thenoyl)pyrrole,
2-methylsulfonyl-5-(1-butyl-2-pyrroyl)pyrrole,
2-methylsulfonyl-5-(1-methyl-2-pyrroyl)pyrrole,
2-methylsulfonyl-5-(2-pyrroyl)pyrrole,
2-methylsulfonyl-5-(4-chlorobenzoyl)pyrrole,
2-methylsulfonyl-5-(3-methoxybenzoyl)pyrrole,
2-methylsulfonyl-5-(2-ethoxycarbonylbenzoyl)pyrrole,
2-methylsulfonyl-5-(2-fluorobenzoyl)pyrrole,
2-methylsulfonyl-5-(3-ethylbenzoyl)pyrrole,
2-methylsulfonyl-5-(4-ethylcarbonylbenzoyl)pyrrole.

EXAMPLE 7

Preparation of 1-[2-(4,6-dioxo-2,2-dimethyl-1,3-dioxan-5-yl)ethyl]-2-methanesulfonyl)-5-(benzoyl)pyrrole (Step 4c)

A. To a stirred suspension of 50% sodium hydride in mineral oil (1.56 g, 48 mmoles) in dry dimethylformamide (100 ml), maintained in an atmosphere of nitrogen, was added the sulfone 2-methylsulfonyl-5-benzoylpyrrole (12.0 g, 48 mmoles), dissolved in dry dimethylformamide (30 ml), over a 5 minute period. When gas evolution had ceased, the cyclopropyl compound spiro[2,5]-5,7-dioxa-6,6-dimethyloctane-4,8-dione (8.16 g, 48 mmoles) was added and the solution was heated at 90° for 4 hours. The cooled solution was diluted with 10% hydrochloric acid solution and the resultant was extracted with ethyl acetate. The extract was washed with water, dried over sodium sulfate and evaporated in vacuo. The residue was subjected to column chromatography on silica gel (600 g) using ethyl acetate-hexane (2:3) as the eluting solvent. In this way there was obtained the starting sulfone (3.0 g, 25%) and the product 1-[2-(4,6-dioxo-2,2-dimethyl-1,3-dioxan-5-yl)ethyl]-2-methanesulfonyl-5-(benzoyl) pyrrole (7.0 g, 35%; 46% based on starting material consumed). Recrystallization of the product was effected from aqueous acetone.

mp: 155°–156° (water-acetone)
UV: 260, 292 nm (ε 10,200, 17,000)
IR: (KBr) 1780, 1746, 1649 cm$^{-1}$
NMR: (Pyridine—d$_5$)

| | |
|---|---|
| 1.62 | (s, 3H) |
| 3.02 | (5, 2H, J = 6.8 Hz) |
| 3.57 | (s, 3H) |
| 5.28 | (5, 2H, J = 6.8 Hz) |
| 6.58 | (d, 1H, J = 4.1 Hz) |
| 7.03 | (d, 1H, J = 4.1 Hz) |
| 7.33–7.51 | (m, 3H) |
| 7.77–7.94 | (m, 2H) |

Calcd. for $C_{20}H_{21}NO_7S$: C, 57.28; H, 5.05; N, 3.34.
Found: C, 57.20; H, 5.25; N, 3.29.

B. Similarly substituting into the procedure of part A for 2-methylsulfonyl-5-benzoylpyrrole the compounds listed in Example 6, part B, one obtains:
[1-[2-(4,6-dioxan-2,2-dimethyl-1,3-dioxan-5-yl)ethyl]-2-(methanesulfonyl)-4-(n-butyl)-5-(benzoyl)]pyrrole,
[1-[2-(4,6-dioxo-2,2-dimethyl-1,3-dioxan-5-yl)ethyl]-2-(methanesulfonyl)-4-(i-propyl)-5-(benzoyl)]pyrrole,
[1-[2-(4,6-dioxo-2,2-dimethyl-1,3-dioxan-5-yl)ethyl]-2-(methanesulfonyl)-4-(methyl)-5-(benzoyl)]pyrrole.

C. Similarly, substituting into the procedure of part A for 2-methylsulfonyl-5-benzoylpyrrole the compounds listed in Example 6, part C, one obtains:
[1-[2-(4,6-dioxo-2,2-dimethyl-1,3-dioxan-5-yl)ethyl]-2-(methanesulfonyl)-5-(3-thenoyl)[pyrrole,
[1-[2-(4,6-dioxo-2,2-dimethyl-1,3-dioxan-5-yl)ethyl]-2-(methanesulfonyl)-5-(2-furoyl)]pyrrole,
[1-[2-(4,6-dioxo-2,2-dimethyl-1,3-dioxan-5-yl)ethyl]-2-(methanesulfonyl)-5-(2-thenoyl)]pyrrole,
[1-[2-(4,6-dioxo-2,2-dimethyl-1,3-dioxan-5-yl)ethyl]-2-(methanesulfonyl)-5-(3-chloro-2-furoyl)[pyrrole,
[1-[2-(4,6-dioxo-2,2-dimethyl-1,3-dioxan-5-yl)ethyl]-2-(methanesulfonyl)-5-(4-bromo-2-furoyl)]pyrrole,
[1-[2-(4,6-dioxo-2,2-dimethyl-1,3-dioxan-5-yl)ethyl]-2-(methanesulfonyl)-5-(5-methyl-2-furoyl)]pyrrole,
[1-[2-(4,6-dioxo-2,2-dimethyl-1,3-dioxan-5-yl)ethyl]-2-(methanesulfonyl)-5-(4-methyl-2-thenoyl)]pyrrole,
[1-[2-(4,6-dioxo-2,2-dimethyl-1,3-dioxan-5-yl)ethyl]-2-(methanesulfonyl)-5-(1-butyl-2-pyrroyl)]pyrrole,
[1-[2-(4,6-dioxo-2,2-dimethyl-1,3-dioxan-5-yl)ethyl]-2-(methanesulfonyl)-5-(1-methyl-2-pyrroyl)]pyrrole,
[1-[2-(4,6-dioxo-2,2-dimethyl-1,3-dioxan-5-yl)ethyl]-2-(methanesulfonyl)-5-(2-pyrroyl)]pyrrole,
[1-[2-(4,6-dioxo-2,2-dimethyl-1,3-dioxan-5-yl)ethyl]-2-(methanesulfonyl)-5-(4-chlorobenzoyl)]pyrrole,
[1-[2-(4,6-dioxo-2,2-dimethyl-1,3-dioxan-5-yl)ethyl]-2-(methanesulfonyl)-5-(3-methoxybenzoyl)]pyrrole,
[1-[2-(4,6-dioxo-2,2-dimethyl-1,3-dioxan-5-yl)ethyl]-2-(methanesulfonyl)-5-(2-ethoxycarbonylbenzoyl)]pyrrole,
[1-[2-(4,6-dioxo-2,2-dimethyl-1,3-dioxan-5-yl)ethyl]-2-(methanesulfonyl)-5-(2-fluorobenzoyl)]pyrrole,
[1-[2-(4,6-dioxo-2,2-dimethyl-1,3-dioxan-5-yl)ethyl]-2-(methanesulfonyl)-5-(3-ethylbenzoyl)]pyrrole,
[1-[2-(4,6-dioxo-2,2-dimethyl-1,3-dioxan-5-yl)ethyl]-2-(methanesulfonyl)-5-(4-ethylcarbonylbenzoyl)]pyrrole.

EXAMPLE 8

Preparation of dimethyl 5-benzoyl-1,2-dihydro-3H-pyrrolo[1,2-a]pyrrole-1,1-dicarboxylate (Step 6)

Sodium hydride in mineral oil (50%, 0.060 g, 1.2 mmoles) was added to a solution of [1-[3,3-(dimethoxycarbonyl)propyl]-2-methanesulfonyl-5-(benzoyl)]pyrrole (0.463 g, 1.13 mmoles) in dry dimethylformamide (25 ml) in a nitrogen atmosphere. After 0.5 hour at room temperature the solution was heated, in an oil bath, at 100°–110° for 2 hours. The progress of the reaction was followed by TLC (ethyl acetate-hexane; 1:3) on silica gel. The solution was cooled to room temperature, water (100 ml) was added, and the solution was made acidic with 0.01 N hydrochloric acid. The products were extracted into ethyl acetate (total of 100 ml), the extract was dried and evaporated in vacuo. Ethereal diazomethane was added to the residue and after removal of the ether and excess diazomethane in vacuo the mixture of esters was subject to column chromatography on silica gel using ethyl acetate-hexane (1:3) as the eluting solvent. In this way there was isolated a mixture of dimethyl 5-benzoyl-1,2-dihydro-3H-pyrrolo[1,2-a]pyrrole-1,1-dicarboxylate and methyl 5-benzoyl-1,2-dihydro-3H-pyrrolo[1,2-a]pyrrole-1-carboxylate acid as an oil (0.210 g) [and starting material (0.097 g, 21%], which was normally used without purification in the next step. The two esters, could, however, be separated by TLC on silica gel using ethyl acetate hexane (1:4) as the developing solvent.

For dimethyl 5-benzoyl-1,2-dihydro-3H-pyrrolo[1,2-a]pyrrole-1,1-dicarboxylate
IR: (CHCl$_3$) 1745, 1740, 1620, 1575(w) cm$^{-1}$.
NMR: (CDCl$_3$)

| | |
|---|---|
| 3.00 | (t, 2H; J = 6.4 Hz) |
| 3.63 | (s, 6H) |
| 4.36 | (t, 2H, J = 6.4) |
| 6.04 | (d, 1H, J = 4) |
| 6.56 | (d, 1H, J = 4) |
| 7.00–7.57 | (m, 5H) |

The methyl 5-benzoyl-1,2-dihydro-3H-pyrrolo[1,2-a]pyrrole-1-carboxylate was also an oil and physical properties essentially identical to an authentic sample prepared by another route.
Calcd. for $C_{19}H_{21}NO_7S$: C, 56.01; H, 5.19; N, 3.43.
Found: C, 55.87; H, 5.25; N, 3.24.

B. Similarly, substituting into the procedure of part A for 1-[3,3-(dimethoxycarbonyl)propyl]-2-methanesulfonyl)-5-(benzoyl) pyrrole the compounds listed in Example 5, part B, one obtains:
dimethyl 4-n-butyl-5-benzoyl-1,2-dihydro-3H-pyrrolo[1,2-a]pyrrole-1,1-dicarboxylate, dimethyl 4-i-butyl-5-benzoyl-1,2-dihydro-3H-pyrrolo[1,2-a]pyrrole-1,1-dicarboxylate,
dimethyl 4-methyl-5-benzoyl-1,2-dihydro-3H-pyrrolo[1,2-a]pyrrole-1,1-dicarboxylate.

C. Similarly, substituting into the procedure of Part A for 1-[3,3-(dimethoxycarbonyl)propyl]-2-methanesulfonyl)-5-(benzoyl) pyrrole the compounds listed in Example 5, part C, one obtains:
dimethyl 5-(3-thenoyl)-1,2-dihydro-3H-pyrrolo[1,2-a]pyrrole-1,1-dicarboxylate,
dimethyl 5-(2-furoyl)-1,2-dihydro-3H-pyrrolo[1,2-a]pyrrole-1,1-dicarboxylate,
dimethyl 5-(2-thenoyl)-1,2-dihydro-3H-pyrrolo[1,2-a]pyrrole-1,1-dicarboxylate,
dimethyl 5-(3-chloro-2-furoyl)-1,2-dihydro-3H-pyrrolo[1,2-a]pyrrole-1,1-dicarboxylate,
dimethyl 5-(4-bromo-2-furoyl)-1,2-dihydro-3H-pyrrolo[1,2-a]pyrrole-1,1-dicarboxylate,
dimethyl 5-(5-methyl-2-furoyl)-1,2-dihydro-3H-pyrrolo[1,2-a]pyrrole-1,1-dicarboxylate,
dimethyl 5-(4-methyl-2-thenoyl)-1,2-dihydro-3H-pyrrolo[1,2-a]pyrrole-1,1-dicarboxylate,
dimethyl 5-(1-butyl-2-pyrroyl)-1,2-dihydro-3H-pyrrolo[1,2-a]pyrrole-1,1-dicarboxylate,
dimethyl 5-(1-methyl-2-pyrroyl)-1,2-dihydro-3H-pyrrolo[1,2-a]pyrrole-1,1-dicarboxylate,
dimethyl 5-(2-pyrroyl)-1,2-dihydro-3H-pyrrolo[1,2-a]pyrrole-1,1-dicarboxylate,
dimethyl 5-(4-chlorobenzoyl)-1,2-dihydro-3H-pyrrolo[1,2-a]pyrrole-1,1-dicarboxylate,
dimethyl 5-(3-methoxybenzoyl)-1,2-dihydro-3H-pyrrolo[1,2-a]pyrrole-1,1-dicarboxylate,
dimethyl 5-(2-ethoxycarbonylbenzoyl)-1,2-dihydro-3H-pyrrolo[1,2-a]pyrrole-1,1-dicarboxylate,
dimethyl 5-(2-fluorobenzoyl)-1,2-dihydro-3H-pyrrolo[1,2-a]pyrrole-1,1-dicarboxylate,
dimethyl 5-(3-ethylbenzoyl)-1,2-dihydro-3H-pyrrolo[1,2-a]pyrrole-1,1-dicarboxylate,
dimethyl 5-(4-ethylcarbonylbenzoyl)-1,2-dihydro-3H-pyrrolo[1,2-a]pyrrole-1,1-dicarboxylate.

EXAMPLE 9

Preparation of
5-benzoyl-1,2-dihydro-3H-pyrrolo[1,2-a]pyrrole-1-carboxylic acid: Decarboxylation of dimethyl 5-benzoyl-1,2-dihydro-3H-pyrrolo[1,2-a]pyrrole-1,1-decarboxylate and simultaneous hydrolysis of methyl 5-benzoyl-1,2-dihydro-3H-pyrrolo[1,2-a]pyrrole-1-carboxylate A. A mixture of two esters (0.273 g) was heated at reflux temperature in water (1 ml) methanol (3 ml) solution with six equivalents of potassium hydroxide for 0.5 hour. The solvent was removed in vacuo, water (50 ml) was added and the solution was made acidic with 10% hydrochloric acid. The product was extracted with ethyl acetate, the extract was washed with water, dried over sodium sulfate, and evaporated in vacuo. The solid residue (0.232 g, 85%) had m.p. 158° and was identical to an authentic specimen of 5-benzoyl-1,2-dihydro-3H-pyrrolo[1,2-a]pyrrole-1-carboxylic acid prepared by another route.

B. Similarly, substituting into the procedure of part A for dimethyl 5-benzoyl-1,2-dihydro-3H-pyrrolo[1,2-a]pyrrole-1,1-dicarboxylate the compounds listed in Example 8, part B, one obtains:
4-n-butyl-5-benzoyl-1,2-dihydro-3H-pyrrolo[1,2-a]pyrrole-1-carboxylic acid,
4-i-propyl-5-benzoyl-1,2-dihydro-3H-pyrrolo[1,2-a]pyrrole-1-carboxylic acid,
4-methyl-5-benzoyl-1,2-dihydro-3H-pyrrolo[1,2-a]pyrrole-1-carboxylic acid.

C. Similarly, substituting into the procedure of part A for dimethyl 5-benzoyl-1,2-dihydro-3H-pyrrolo[1,2-a]pyrrole-1,1-dicarboxylate the compounds listed in Example 8, part C, one obtains:
5-(3-thenoyl)-1,2-dihydro-3H-pyrrolo[1,2-a]pyrrolo-1-carboxylic acid,
5-(2-furoyl)-1,2-dihydro-3H-pyrrolo[1,2-a]pyrrolo-1-carboxylic acid,
5-(2-thenoyl)-1,2-dihydro-3H-pyrrolo[1,2-a]pyrrolo-1-carboxylic acid,
5-(3-chloro-2-furoyl)-1,2-dihydro-3H-pyrrolo[1,2-a]pyrrolo-1-carboxylic acid,
5-(4-bromo-2-furoyl)-1,2-dihydro-3H-pyrrolo[1,2-a]pyrrolo-1-carboxylic acid,
5-(5-methyl-2-furoyl)-1,2-dihydro-3H-pyrrolo[1,2-a]pyrrolo-1-carboxylic acid,
5-(4-methyl-2-thenoyl)-1,2-dihydro-3H-pyrrolo[1,2-a]pyrrolo-1-carboxylic acid,
5-(1-butyl-2-pyrroyl)-1,2-dihydro-3H-pyrrolo[1,2-a]pyrrolo-1-carboxylic acid,
5-(1-methyl-2-pyrroyl)-1,2-dihydro-3H-pyrrolo[1,2-a]pyrrolo-1-carboxylic acid,
5-(2-pyrroyl)-1,2-dihydro-3H-pyrrolo[1,2-a]pyrrolo-1-carboxylic acid,
5-(4-chlorobenzoyl)-1,2-dihydro-3H-pyrrolo[1,2-a]pyrrolo-1-carboxylic acid,
5-(3-methoxybenzoyl)-1,2-dihydro-3H-pyrrolo[1,2-a]pyrrolo-1-carboxylic acid,
5-(2-ethoxycarbonylbenzoyl)-1,2-dihydro-3H-pyrrolo[1,2-a]-pyrrolo-1-carboxylic acid,
5-(2-fluorobenzoyl)-1,2-dihydro-3H-pyrrolo[1,2-a]pyrrolo-1-carboxylic acid,
5-(3-ethylbenzoyl)-1,2-dihydro-3H-pyrrolo[1,2-a]pyrrolo-1-carboxylic acid,
5(4-ethylcarbonylbenzoyl)-1,2-dihydro-3H-pyrrolo[1,2-a]-pyrrolo-1-carboxylic acid.

EXAMPLE 10

Preparation of
2-(methylthio)-5-(4-fluorobenzoyl)pyrrole (Step 2)

A solution of N,N-dimethyl-4-fluorobenzamide (8.4 g, 0.05 moles) in anhydrous 1,2-dichloroethane (170 ml) containing phosphorous oxychloride (7.7 g, 0.05 moles) was heated at reflux temperature for 1 hour. At the end of this time 2-methylthiopyrrole (2.82 g, 0.025 moles) was added and heating was continued for an additional 0.5 hour. The solution was cooled to room temperature, and to the cooled solution was cautiously added, with good agitation, a solution of sodium acetate (12.3 g, 0.15 moles) in water (50 ml) and the mixture was then boiled under reflux for 1 hour. The organic phase was separated, washed with water, dried, and evaporated. The residue was subjected to column chromatography on silica gel using ethyl acetate-hexane (1:9) as the eluting solvent. A yellow colored solid 2-(methylthio)-5-(4-fluorobenzoyl)pyrrole (3.2 g, 54%) was obtained which after crystallization from ether-hexane had m.p. 112°–113° C.

UV: (MeOH) 218.5, 248, 343 nm($\epsilon$9770, 8510, 13,800).
IR: (CHCl$_3$) 3440, 3250, 1610 cm$^{-1}$.
NMR: (CDCl$_3$)

| | |
|---|---|
| 2.48 | (s, 3H) |
| 6.25 | (q, 1H; J = 2.5, 4 Hz) |
| 6.80 | (q, 1H; J = 2.5, 4 Hz) |
| 7.12 | (q, 2H; J = 8) |
| 7.92 | (q, 2H; J = 5.5, 8) |
| 10.67 | (s, 1H; WH = 22) |

Calcd. for $C_{12}H_{10}FNOS$: C, 61.24; H, 4.28.
Found: C, 61.01; H, 4.21.

EXAMPLE 11

Preparation of
1-[[2-(4,6-dioxo-2,2-dimethyl-1,3-benzodioxan-5-yl)ethyl]-2-(methylthio)-5-(4-fluorobenzoyl)]pyrrole (Step 3a or 3b)

A (0.227 g, 0.97 mmoles) was added to a suspension of 50% sodium hydride in mineral oil (0.054 g, 1.0 mmoles) in dry dimethylformamide (15 ml) 2-(methylthio)-5-(4-fluorobenzoyl)pyrrole and stirred at room temperature, in an argon atmosphere for 0.5 hour. Compound J, spiro[2,5]-5,7-dioxa-6,6-dimethyloctane-4,8-dione (0.181 g, 1.07 mmoles) was then added and the mixture was heated in an oil bath at 65° for 1.5 hours. The solution was cooled to room temperature, water (150 ml) was added and the starting material was extracted into ethyl acetate. The extract was washed with water, dried over sodium sulfate and evaporated in vacuo to give the unconsumed reactant (0.050 g, 22%). The aqueous phase from above was made acidic with 0.01 N hydrochloric acid, the products were extracted into ethyl acetate and the extract was dried and evaporated. The residue (0.434 g) was subjected to column chromatography on silica gel using ethyl acetate-hexane-methanol (9:10:1) as the eluting solvent. The product (0.284 g, 56%) and a slightly more polar substance (0.030 g) were isolated. In another reaction, using the same conditions, but a freshly opened can of sodium hydride, a 72% yield of the desired product was obtained.

Crystallization of the product from ethyl acetate hexane gave material 1-[[2-(4,6-dioxo-2,2-dimethyl-1,3-benzodioxan-5-yl)ethyl]-2-(methylthio)-5-(4-fluorobenzoyl)]pyrrole m.p. 92°, which was isolated as the monohydrate.

UV: (MeOH) 217, 265.5, 340 nm($\epsilon$5370, 8130, 7760).
IR: (CHCl$_3$) 1795, 1755, 1620 1600 cm$^{-1}$.
NMR: (CDCl$_3$).

| | |
|---|---|
| 1.77 | (s, 3H) |
| 1.82 | (S, 3H) |
| 2.50 | (s, 3H) |
| 2.4–2.8 | (m, 2H) |
| 4.15 | (t, 1H; J = 5.5, Hz) |
| 4.70 | (t, 2H; J = 6) |
| 6.17 | (d, 1H; J = 4) |
| 6.68 | (d, 1H; J = 4) |
| 7.05 | (q, 2H; J = 8, 8) |
| 7.72 | (q, 2H; J = 6, 8) |

Calcd. for $C_{20}H_{20}FNO_5S \cdot H_2O$: C, 56.72; H, 5.24; N, 3.31.
Found: C, 56.84; H, 5.15; N, 3.24.

EXAMPLE 12

Preparation of
[1-[3,3-(dimethoxycarbonyl)propyl]-2-(methylthio)-5-(4-fluorobenzoyl)]pyrrole (Step 4a)

To a solution of 1-[[2-(4,6-dioxo-2,2-dimethyl-1,3-benzodioxan-5-yl)ethyl]-2-(methylthio)-5-(4-fluorobenzoyl)]pyrrole (0.50 g) in methanol (15 ml) was added methanol which had been saturated with hydrogen chloride gas (15 ml). The solution was heated at reflux temperature for 0.5 hour and the solvent was then removed in vacuo. The residue was then percolated through a column of silica gel using ethyl acetate-hexane (1:4) as the percolating solent. The produce [1-[3,3-(dimethoxycarbonyl)propyl]-2-(methylthio)-5-(4-fluorobenzoyl)]pyrrole was obtained as an oil.

UV: (MeOH) 215, 248, 334 nm($\epsilon$10,000, 8510, 14,500).
IR: (CHCl$_3$) 1755, 1735, 1620, 1600 cm$^{-1}$.
MS: 393 (M+).
NMR: (CDCl$_3$)

| | |
|---|---|
| 2.47 | (s, 3H) |
| 2.20–2.65 | (m, 2H) |
| 3.48 | (t, 1H; J = 7 Hz) |
| 3.72 | (s, 6H) |
| 4.58 | (t, 2H; J = 7) |
| 6.17 | (d, 1H; J = 4) |
| 6.67 | (d, 1H; J = 4) |
| 7.07 | (q, 2H; J = 8, 5, 8.5) |
| 7.75 | (q, 2H; J = 5.5, 8.5). |

B. Similarly, substituting into the procedure of part A for 1-[2-(4,6-dioxo-2,2-dimethyl-1,3-benzodioxan-5-yl)-ethyl]-2-(methylthio)-5-(4-fluorobenzoyl) pyrrole the compounds listed in Example 3, part B, one obtains:
[1-[3,3-(dimethoxycarbonyl)propyl]-2-(methylthio)-4-(n-butyl)-5-(benzoyl)]pyrrole,
[1-[3,3-(dimethoxycarbonyl)propyl]-2-(methylthio)-4-(i-propyl)-5-(benzoyl)]pyrrole,
[1-[3,3-(dimethoxycarbonyl)propyl]-2-methylthio)-4-(methyl)-5-(benzoyl)]pyrrole.

C. Similarly, substituting into the procedure of part A for 1-[2-(4,6-dioxo-2,2-dimethyl-1,3-benzodioxan-5-yl)-ethyl]-2-(methylthio)-5-(4-fluorobenzoyl)pyrrole the compounds listed in Example 3, part C, one obtains:
[1-[3,3-(dimethoxycarbonyl)propyl]-2-(methylthio)-5-(3-thenoyl)]pyrrole,
[1-[3,3-(dmethoxycarbonyl)propyl]-2-(methylthio)-5-(2-furoyl)]pyrrole,
[1-[3,3-(dimethoxycarbonyl)propyl]-2-(methylthio)-5-(2-thenoyl)]pyrrole,
[1-[3,3-(dimethoxycarbonyl)propyl]-2-(methylthio)-5-(3-chloro-2-furoyl)]pyrrole,
[1-[3,3-(dimethoxycarbonyl)propyl]-2-(methylthio)-5-(4-bromo-2-furoyl)]pyrrole,
[1-[3,3-(dimethoxycarbonyl)propyl]-2-(methylthio)-5-(5-methyl-2-furoyl)]pyrrole,
[1-[3,3-(dimethoxycarbonyl)propyl]-2-(methylthio)-5-(4-methyl-2-thenoyl)]pyrrole,
[1-[3,3-(dimethoxycarbonyl)propyl]-2-(methylthio)-5-(1-butyl-2-pyrroyl)]pyrrole,
[1-[3,3-(dimethoxycarbonyl)propyl]-2-(methylthio)-5-(1-methyl-2-pyrroyl)]pyrrole,
[1-[3,3-(dimethoxycarbonyl)propyl]-2-(methylthio)-5-(2-pyrroyl)]pyrrole,
[1-[3,3-(dimethoxycarbonyl)propyl]-2-(methylthio)-5-(4-chlorobenzoyl)]pyrrole,

[1-[3,3-(dimethoxycarbonyl)propyl]-2-(methylthio)-5-(3-methoxybenzoyl)]pyrrole,
[1-[3,3-(dimethoxycarbonyl)propyl]-2-(methylthio)-5-(2-ethoxycarbonylbenzoyl)]pyrrole,
[1-[3,3-(dimethoxycarbonyl)propyl]-2-(methylthio)-5-(2-fluorobenzoyl)]pyrrole,
[1-[3,3-(dimethoxycarbonyl)propyl]-2-(methylthio)-5-(3-ethylbenzoyl)]pyrrole,
[1-[3,3-(dimethoxycarbonyl)propyl]-2-(methylthio)-5-(4-ethylcarbonylbenzoyl)]pyrrole.

EXAMPLE 13

Preparation of
[1-[3,3-(dimethoxycarbonyl)propyl]-2-methanesulfonyl-5-(4-fluorobenzoyl)]pyrrole (Step 5a)

A. A solution of [1-[3,3-(dimethoxycarbonyl)propyl]-2-(methylthio)-5-(4-fluorobenzoyl)]pyrrole (0.700 g, 1.5 mmoles) in dry dichloromethane (50 ml) containing 85% m-chloroperbenzoic acid (0.700 g, 4 mmoles) was cooled in an ice bath and after 1 hours TLC (dimethylethane-dioxan-acetic acid, 70:30:1) indicated that only the sulfone [1-[3,3-(dimethoxycarbonyl)propyl]-2-methanesulfonyl-5-(4-fluorobenzoyl)]pyrrole was present. The solvent was removed in vacuo, the residue was shaken with 10% sodim dicarbonate solution and the product was extracted into ether. The extract was washed with water, dried, and evaporated. The residue was subjected to column chromatography on silica gel using ethyl acetate-hexane (3:7) as the eluant. The product, [1-[3,3-(dimethoxycarbonyl)propyl]-2-methanesulfonyl-5-(4-fluorobenzoyl)]pyrrole, was obtained as an oil (0.558 g, 80%).

UV: (MeOH) 219, 259, 291.5 nm($\epsilon$8510, 8710, 13,500).
IR: (CHCl$_3$) 1755, 1735, 1650, 1600, 1325, 1145, 1125 cm$^{-1}$.
NMR: (CDCl$_3$)

| | |
|---|---|
| 2.42 | (m, 2H) |
| 3.23 | (s, 3H) |
| 3.4–3.8 | (m, 1H) |
| 3.75 | (s, 6H) |
| 4.78 | (m, 2H) |
| 6.65 | (d, 1H; J = 4 Hz) |
| 6.92 | (d, 1H; J = 4) |
| 6.95–8.10 | (m, 4H) |

Calcd. for C$_{19}$H$_{20}$FNO$_7$S: C, 53.64; H, 4.74; N, 3.29. Found: C, 53.82; H, 4.91; N, 3.06.

B. Similarly, substituting into the procedure of part A for 1-[3,3-(dimethoxycarbonyl)propyl]-2-(methylthio)-5-(4-fluorobenzoyl) pyrrole the compounds listed in Example 12, part B, one obtains:
[1[3,3-(dimethoxycarbonyl)propyl]-2-methanesulfonyl-4-n-butyl-5-benzoyl]pyrrole,
[1[3,3-(dimethoxycarbonyl)propyl]-2-methanesulfonyl-4-i-propyl-5-benzoyl]pyrrole,
[1[3,3-(dimethoxycarbonyl)propyl]-2-methanesulfonyl-4-methyl-5-benzoyl]pyrrole.

C. Similarly, substituting into the procedure of part A for 1-[3,3-(dimethoxycarbonyl)propyl]-2-(methylthio)-5-(4-fluorobenzoyl) pyrrole one obtains:
[1-[3,3-(dimethoxycarbonyl)propyl]-2-methanesulfonyl-5-(3-thenoyl)]pyrrole,
[1-[3,3-(dimethoxycarbonyl)propyl]-2-methanesulfonyl-5-(2-furoyl)]pyrrole,
[1-[3,3-(dimethoxycarbonyl)propyl]-2-methanesulfonyl-5-(2-thenoyl)]pyrrole,
[1-[3,3-(dimethoxycarbonyl)propyl]-2-methanesulfonyl-5-(3-chloro-2-furoyl)]pyrrole,
[1-[3,3-(dimethoxycarbonyl)propyl]-2-methanesulfonyl-5-(4-bromo-2-furoyl)]pyrrole,
[1-[3,3-(dimethoxycarbonyl)propyl]-2-methanesulfonyl-5-(5-methyl-2-furoyl)]pyrrole,
[1-[3,3-(dimethoxycarbonyl)propyl]-2-methanesulfonyl-5-(4-methyl-2-thenoyl)]pyrrole,
[1-[3,3-(dimethoxycarbonyl)propyl]-2-methanesulfonyl-5-(1-butyl-2-pyrroyl)]pyrrole,
[1-[3,3-(dimethoxycarbonyl)propyl]-2-methanesulfonyl-5-(1-methyl-2-pyrroyl)]pyrrole,
[1-[3,3-(dimethoxycarbonyl)propyl]-2-methanesulfonyl-5-(2-pyrroyl)]pyrrole,
[1-[3,3-(dimethoxycarbonyl)propyl]-2-methanesulfonyl-5-(4-chlorobenzoyl)]pyrrole,
[1-[3,3-(dimethoxycarbonyl)propyl]-2-methanesulfonyl-5-(3-methoxybenzoyl)]pyrrole,
[1-[3,3-(dimethoxycarbonyl)propyl]-2-methanesulfonyl-5-(2-ethoxycarbonylbenzoyl)]pyrrole,
[1-[3,3-(dimethoxycarbonyl)propyl]-2-methanesulfonyl-5-(2-fluorobenzoyl)]pyrrole,
[1-[3,3-(dimethoxycarbonyl)propyl]-2-methanesulfonyl-5-(3-ethylbenzoyl)]pyrrole,
[1-[3,3-(dimethoxycarbonyl)propyl]-2-methanesulfonyl-5-(4-ethylcarbonylbenzoyl)]pyrrole.

EXAMPLE 14

Preparation of dimethyl 5-(4-fluorobenzoyl)-1,2-dihydro-3H-pyrrolo-[1,2-a]pyrrole-1,1-dicarboxylate (Step 6)

Sodium hydride in mineral oil (50%, 0.048 g, 1 mmole) was added, under a nitrogen atmosphere, to a solution of (0.483 g, 0.8 mmoles) in dry dimethylformamide (30 ml). After 1 hour at room temperature, the reaction was placed in an oil bath at 90° for 4 hours. The reaction progress was followed by TLC on silica gel (ethyl acetate-hexane; 1.3). Water was added to the cooled solution and the product was extracted with ethyl acetate. The extract was washed with water, dried and evaporated. The residue was treated with excess ethereal diazomethane and after removal of the solvent the product mixture was subjected to column chromatography on silica gel using ethyl acetate-hexane (1:4) as the eluting solvent. In this way an oily mixture of dimethyl 5-(4-fluorobenzoyl)-1,2-dihydro-3H-pyrrolo[1,2-a]pyrrole-1,1-dicarboxylate and methyl 5-(4-fluorobenzoyl)-1,2-dihydro-3H-pyrrolo[1,2-a]pyrrole-1-carboxylate (0.145 g) and the starting material (0.080 g, 23%) were obtained.

EXAMPLE 15

Preparation of
5-(4-fluorobenzoyl)-1,2-dihydro-3H-pyrrolo[1,2-a]-pyrrole-1-carboxylic acid: Decarboxylation of dimethyl 5-(4-fluorobenzoyl)1,2-dihydro-3H-pyrrolo[1,2-a]pyrrole-1,1-dicarboxylate and simultaneous hydrolysis of methyl 5-(4-fluorobenzoyl)-1,2-dihydro-3H-pyrrolo[1,2-a]pyrrole-1-carboxylate (Decarboxylation step)

A solution of the mixture of dimethyl 5-(4-fluorobenzoyl)-1,2-dihydro-3H-pyrrolo[1,2-a]pyrrole-1,1-dicarboxylate and methyl 5-(4-fluorobenzoyl)-1,2-dihydro-3H-pyrrolo[1,2-a]pyrrole-1-carboxylate (0.200 g) in methanol (5 ml) and water (3 ml) containing potassium hydroxide (0.5 g) was heated at reflux temperature for 1 hour. The solvent was removed in vacuo, water was added to the residue and the solution was made acidic with 10% hydrochloric acid solution. The product was extracted into ethyl acetate, the extract was dried and evaporated. The solid residue on crystallization from ethyl acetate-hexane gave 5-(4-fluorobenzoyl)-1,2-dihydro-3H-pyrrolo[1,2-a]pyrrole-1-carboxylic acid (0.124 g, 80%) m.p. 163°. A mixed m.p. with an authentic specimen (m.p. 170°) had m.p. 165°. The IR spectrum was identical to that of the authentic sample.

What is claimed is:

1. A process for preparing a compound of the formula

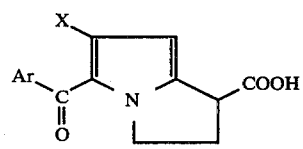 (I)

wherein:

X is hydrogen or lower alkyl; Ar is a moiety selected from the group consisting of

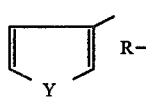, 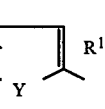, 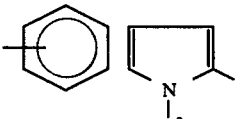 and 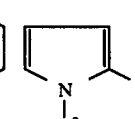

(IA), (IB), (IC) and (ID)

in which:

Y is oxygen or sulfur;

R is hydrogen, methyl, chloro, or bromo;

$R^1$ is hydrogen, lower alkyl, lower alkoxyl, lower alkoxycarbonyl, lower alkylcarbonyl, fluoro, chloro or bromo, $R^2$ is hydrogen or lower alkyl; which comprises decarboxylating a compound represented by the formula

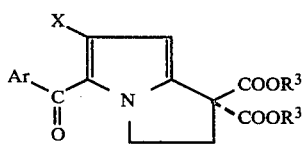 (II)

wherein X and Ar are as defined previously, and $R^3$ is hydrogen or lower alkyl.

2. The process of claim 1 wherein said decarboxylation comprises treating the compound of formula II with acid.

3. The process of claim 2 wherein the acid is a strong mineral acid.

4. The process of claim 1 wherein said decarboxylation comprises treating the compound of formula II with base, and subsequently treating the resultant intermediate with acid.

5. The process of claim 4 wherein the base is a strong mineral base, and the acid is a strong mineral acid.

6. The process of claim 1 wherein the compound represented by formula II is prepared by cyclizing a compound of the formula

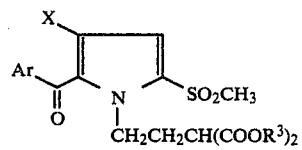 (H)

wherein Ar and X are as previously defined and $R^3$ is lower alkyl.

7. The process of claim 6 wherein said cyclization is effected by treating the compound of formula H with an alkali metal hydride in an aprotic solvent.

8. The process of claim 6 wherein the compound of Formula H is prepared by oxidizing a compound of the formula

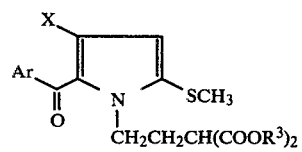 (F)

wherein Ar, X and $R_3$ are as defined in claim 6.

9. The process of claim 8 wherein the oxidizing agent is m-chloroperbenzoic acid.

10. The process of claim 8 wherein the compound of Formula F is prepared by treating a compound of the formula

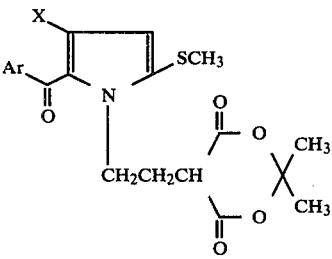 (D)

with a lower alkyl alcohol in the presence of acid.

11. The process of claim 10 wherein the compound of Formula D is prepared by treating of a compound of the formula

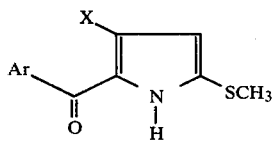 (C)

with an alkali metal hydride in an aprotic organic solvent, followed by treatment with spiro[2,5]-5,7-dioxa-6,6-dimethyloctane-4,8-dione.

12. The process of claim 11 wherein the compound of Formula C is prepared by reacting a compound of the formula

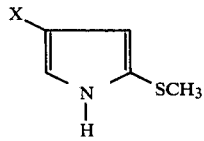 (B)

wherein X is as previously defined, with a compound of the formula

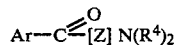

and $R^4$ is lower alkyl in the presence of a halogenating agent.

13. The process of claim 12 wherein the compound of formula B is prepared by reacting a compound of the formula

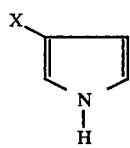

with N-halosuccinimide and dimethylsulfide.

14. The process of claim 13 wherein X is hydrogen or methyl, and Ar is thien-2-yl, furan-2-yl, pyrrol-2-yl or optionally substituted phenyl.

15. The process of claim 13 wherein the compound of Formula I is 5-benzoyl-1,2-dihydro-3H-pyrrolo[1,2-a]pyrrole-1-carboxylic acid.

16. The process of claim 6 wherein the compound of Formula H is prepared by treating a compound of the formula

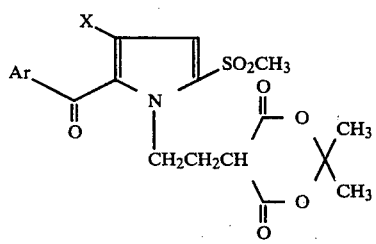

with a lower alkyl alcohol in the presence of acid.

17. The process of claim 16 wherein the compound of Formula G is prepared by oxidizing a compound of the formula

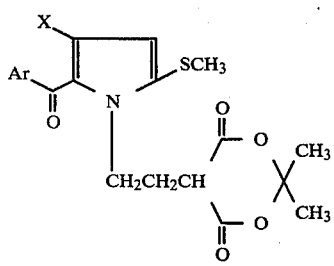

18. The process of claim 17 wherein the oxidizing agent is m-chloroperbenzoic acid.

19. The process of claim 17 wherein the compound of Formula D is prepared by treating a compound of the formula

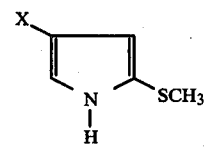

with an alkali metal hydride in an aprotic organic solvent, followed by treatment with spiro[2,5]-5,7-dioxa-6,6-dimethyloctane-4,8-dione.

20. The process of claim 19 wherein the compound of Formula C is prepared by reacting a compound of the formula

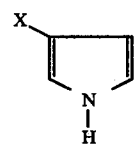

with a compound of the formula

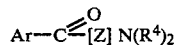

and $R^4$ is lower alkyl in the presence of a halogenating agent.

21. The process of claim 20 wherein the compound of formula B is prepared by reacting a compound of the formula

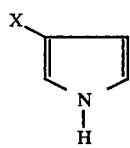

with N-halosuccinimide and dimethylsulfide.

22. The process of claim 21 wherein X is hydrogen or methyl, and Ar is thien-2-yl, furan-2-yl, pyrrol-2-yl or optionally substituted phenyl.

23. The process of claim 21 wherein the compound of Formula I is 5-benzoyl-1,2-dihydro-3H-pyrrolo[1,2-a]pyrrole-1-carboxylic acid.

24. The process of claim 16, wherein the compound of Formula G is prepared by treating a compound of the formula

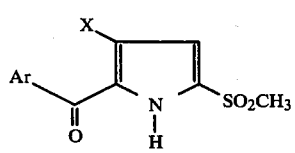

with an alkali metal hydride in an aprotic organic solvent, followed by treatment with spiro[2,5]-5,7-dioxa-6,6-dimethyloctane-4,8-dione.

25. The process of claim 24, wherein the compound of Formula E is prepared by oxidizing a compound of the formula

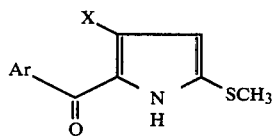

(C)

26. The process of claim 25 wherein the oxidizing agent is m-chloroperbenzoic.

27. The process of claim 25 wherein the compound of formula C is prepared by reacting a compound of the formula

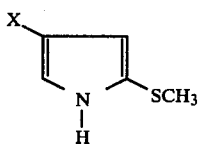

(B)

wherein X is as previously defined, with a compound of the formula

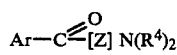

and R⁴ is lower alkyl in the presence of a halogenating agent.

28. The process of claim 27 wherein the compound of formula B is prepared by reacting a compound of the formula

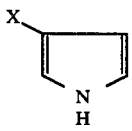

(A)

with N-halosuccinimide and dimethylsulfide.

29. The process of claim 28 wherein X is hydrogen or methyl, and Ar is thien-2-yl, furan-2-yl, pyrrol-2-yl or optionally substituted phenyl.

30. The process of claim 28 wherein the compound of Formula I is 5-benzoyl-1,2-dihydro-3H-pyrrolo[1,2-a]pyrrole-1-carboxylic acid.

31. The process of claim 1 wherein X is hydrogen or methyl, and Ar is thien-2-yl, furan-2-yl, pyrrol-2-yl or optionally substituted phenyl.

32. The process of claim 1 wherein the compound of Formula I is 5-benzoyl-1,2-dihydro-3H-pyrrolo[1,2-a]pyrrole-1-carboxylic acid.

33. A process for preparing a compound of the formula

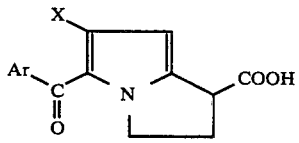

(I)

wherein:
X is hydrogen or lower alkyl; Ar is a moiety selected from the group consisting of

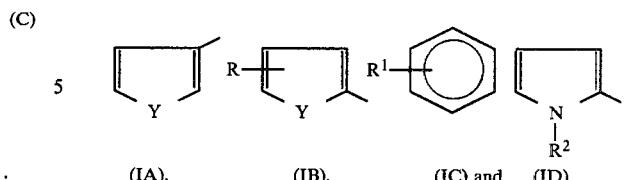

(IA), (IB), (IC) and (ID)

in which:
Y is oxygen or sulfur;
R is hydrogen, methyl, chloro, or bromo;
R¹ is hydrogen, lower alkyl, lower alkoxyl, carboxyl, lower alkoxycarbonyl, lower alkylcarbonyl, fluoro, chloro or bromo;
R² is hydrogen or lower alkyl; which comprises
(a) treating a compound of the formula

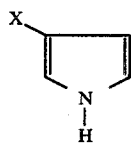

(A)

wherein X is as previously defined, with N-halosuccinimide and dimethylsulfide, followed by
(b) treating the resulting intermediate with a compound of the formula

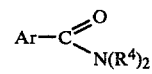

wherein Ar is as previously defined and R⁴ is lower alkyl in the presence of a halogenating agent, followed by
(c) treating the resulting intermediate with an alkali metal hydride in an aprotic organic solvent, followed by treatment with spiro[2,5]-5,7-dioxa-6,6-dimethyloctane-4,8-dione followed by
(d) treating the resulting intermediate with an oxidizing agent, followed by
(e) treating the resulting intermediate with a lower alkyl alcohol in the presence of acid
(f) treating the resulting intermediate with an alkali metal hydride in an aprotic solvent, followed by
(g) treating the resulting intermediate with a base followed by
(h) treating the resulting intermediate with acid.

34. A process for preparing a compound of the formula

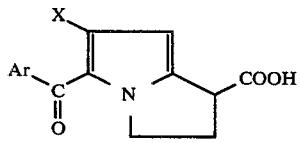

(I)

wherein:
X is hydrogen or lower alkyl; Ar is a moiety selected from the group consisting of

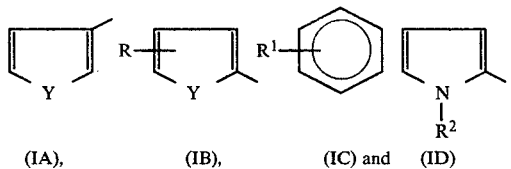

(IA), (IB), (IC) and (ID)

in which:

Y is oxygen or sulfur;

R is hydrogen, methyl, chloro, or bromo;

$R^1$ is hydrogen, lower alkyl, lower alkoxyl, carboxyl, lower alkoxycarbonyl, lower alkylcarbonyl, fluoro, chloro or bromo;

$R^2$ is hydrogen or lower alkyl; which comprises (a) treating a compound of the formula

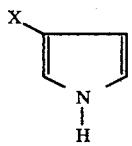

(A)

wherein X is as previously defined, with N-halosuccinimide and dimethylsulfide, followed by (b) treating the resulting intermediate with a compound of the formula

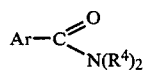

wherein Ar is as previously defined and $R^4$ is lower alkyl in the presence of a halogenating agent, followed by (c) treating the resulting intermediate with an alkali metal hydride in an aprotic organic solvent, followed by treatment with spiro[2,5]-5,7-dioxa-6,6-dimethyloctane-4,8-dione followed by (d) treating the resulting intermediate with a lower alkyl alcohol in the presence of acid followed by (e) treating the resulting intermediate with an oxidizing agent followed by (f) treating the resulting intermediate with an alkali metal hydride in an aprotic solvent, followed by (g) treating the resulting intermediate with a base followed by (h) treating the resulting intermediate with acid.

35. A process for preparing a compound of the formula

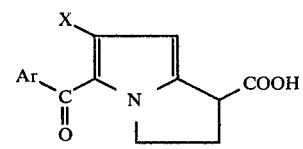

(I)

wherein:

X is hydrogen or lower alkyl; Ar is a moiety selected from the group consisting of

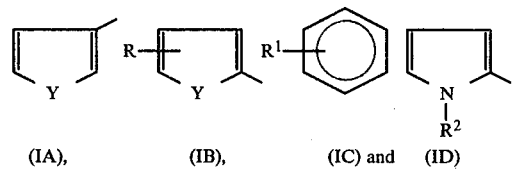

(IA), (IB), (IC) and (ID)

in which:

Y is oxygen or sulfur;

R is hydrogen, methyl, chloro, or bromo;

$R^1$ is hydrogen, lower alkyl, lower alkoxyl, carboxyl, lower alkoxycarbonyl, lower alkylcarbonyl, fluoro, chloro or bromo;

$R^2$ is hydrogen or lower alkyl; which comprises (a) treating a compound of the formula

(A)

wherein X is as previously defined, with N-halosuccinimide and dimethylsulfide, followed by (b) treating the resulting intermediate with a compound of the formula

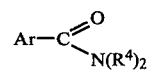

wherein Ar is as previously defined and $R^4$ is lower alkyl in the presence of a halogenating agent, followed by (c) treating the resulting intermediate with an oxidizing agent, followed by (d) treating the resulting intermediate with an alkali metal hydride in an aprotic organic solvent, followed by treatment with spiro[2,5]-5,7-dioxa-6,6-dimethyloctane-4,8-dione followed by (e) treating the resulting intermediate with an oxidizing agent, followed by (f) treating the resulting intermediate with a lower alkyl alcohol in the presence of acid (g) treating the resulting intermediate with an alkali metal hydride in an aprotic solvent, followed by (h) treating the resulting intermediate with a base followed by (i) treating the resulting intermediate with acid.

* * * * *